(12) United States Patent
Furtaw (10) Patent No.: US 10,126,264 B2
(45) Date of Patent: Nov. 13, 2018

(54) ANALYTE SEPARATOR WITH ELECTROHYDRODYNAMIC TAYLOR CONE JET BLOTTER

(71) Applicant: LI-COR, Inc., Lincoln, NE (US)

(72) Inventor: Michael D. Furtaw, Lincoln, NE (US)

(73) Assignee: LI-COR, Inc., Lincoln, NE (US)

( * ) Notice: Subject to any disclaimer, the term of this patent is extended or adjusted under 35 U.S.C. 154(b) by 53 days.

(21) Appl. No.: 14/791,023

(22) Filed: Jul. 2, 2015

(65) Prior Publication Data

US 2016/0011149 A1    Jan. 14, 2016

Related U.S. Application Data

(60) Provisional application No. 62/024,256, filed on Jul. 14, 2014.

(51) Int. Cl.
*G01N 27/447* (2006.01)

(52) U.S. Cl.
CPC . *G01N 27/44791* (2013.01); *G01N 27/44739* (2013.01)

(58) Field of Classification Search
CPC ....... G01N 27/44739; G01N 27/44704; G01N 27/44717–27/44752; G01N 27/44791
See application file for complete search history.

(56) References Cited

U.S. PATENT DOCUMENTS

| 4,631,120 A | 12/1986 | Pohl |
| 4,885,076 A | 12/1989 | Smith et al. |
| 5,094,594 A | 3/1992 | Brennan et al. |
| 5,234,559 A | 8/1993 | Collier et al. |
| 5,275,710 A | 1/1994 | Gombocz et al. |
| 5,393,975 A | 2/1995 | Hail et al. |
| 5,423,964 A * | 6/1995 | Smith ............... G01N 27/44717 204/452 |
| 5,868,322 A | 2/1999 | Loucks et al. |
| 5,916,429 A | 6/1999 | Brunk et al. |
| 6,179,584 B1 | 1/2001 | Howitz et al. |

(Continued)

FOREIGN PATENT DOCUMENTS

| JP | 3775305 | 5/2006 |
| WO | 2017136284 | 8/2017 |
| WO | 2018031483 A1 | 2/2018 |

OTHER PUBLICATIONS

S. K. Back, et al., Capillary Electrophoresis with Nanoparticle Matrix for DNA Analysis, Bull. Korean Chem. Soc., vol. 27, No. 1, pp. 133-136 (2006).*

(Continued)

*Primary Examiner* — Maris R Kessel
(74) *Attorney, Agent, or Firm* — Kilpatrick Townsend & Stockton LLP (57) ABSTRACT

Devices, systems, and methods are disclosed that analyze a biological or other fluid sample using an electrophoresis or other separation method and then emit the fluid sample with separated constituents using an electrohydrodynamic spray to form a Taylor cone and jet, without dispersion into droplets, onto a substrate that moves with respect to the emitter. Electrodes can be shared between the electrophoresis and electrospray elements, and an adjunct fluid can help draw the separated sample into the Taylor cone. A micro-machined capillary channel on a chip can supply multiple lines to a substrate.

18 Claims, 9 Drawing Sheets

(56) References Cited

U.S. PATENT DOCUMENTS

| | | | |
|---|---|---|---|
| 6,602,391 | B2 | 8/2003 | Serikov et al. |
| 6,633,031 | B1* | 10/2003 | Schultz .............. G01N 30/7266 |
| | | | 210/198.2 |
| 6,787,313 | B2 | 9/2004 | Morozova et al. |
| 6,830,934 | B1 | 12/2004 | Harding et al. |
| 7,759,639 | B2 | 7/2010 | Schlaf et al. |
| 7,784,911 | B2 | 8/2010 | Kim et al. |
| 8,293,337 | B2 | 10/2012 | Bhatnagar et al. |
| 8,294,119 | B2 | 10/2012 | Arscott et al. |
| 8,470,570 | B2 | 6/2013 | Kim et al. |
| 9,182,371 | B2 | 11/2015 | Kennedy et al. |
| 9,465,014 | B2 | 10/2016 | Dovichi et al. |
| 2002/0197622 | A1 | 12/2002 | McDevitt et al. |
| 2004/0058423 | A1 | 3/2004 | Albritton et al. |
| 2004/0247450 | A1 | 12/2004 | Kutchinsky et al. |
| 2006/0192107 | A1 | 8/2006 | DeVoe et al. |
| 2007/0035587 | A1 | 2/2007 | Lee et al. |
| 2007/0039866 | A1 | 2/2007 | Schroeder et al. |
| 2013/0032031 | A1* | 2/2013 | Bartko ................. G01N 1/2202 |
| | | | 96/18 |
| 2013/0140180 | A1* | 6/2013 | Dovichi ........... G01N 27/44743 |
| | | | 204/451 |
| 2013/0213811 | A1 | 8/2013 | Kennedy et al. |
| 2013/0327936 | A1 | 12/2013 | Ramsey et al. |
| 2015/0233877 | A1 | 8/2015 | Sun et al. |
| 2015/0279648 | A1 | 10/2015 | Furtaw et al. |
| 2017/0219522 | A1 | 8/2017 | Furtaw |
| 2018/0036729 | A1 | 2/2018 | Furtaw et al. |
| 2018/0036730 | A1 | 2/2018 | Furtaw et al. |

OTHER PUBLICATIONS

International Searching Authority, PCT International Search Report and Written Opinion dated Sep. 30, 2015 for PCT/US2015/039121, 17 pages.

Amantonico et al., "Facile analysis of metabolites by capillary electrophoresis coupled to matrix-assisted laser desorption/ionization mass spectrometry using target plates with polysilazane nanocoating and grooves," Analyst, 2009, vol. 134, vol. 1536-1540.

Anderson et al., "Western Blotting Using Capillary Electrophoresis," Anal. Chem., 2011, vol. 83, pp. 1350-1355.

Avseenko et al., "Immobilization of Proteins in Immunochemical Microarrays Fabricated by Electrospray Deposition," Anal. Chem., 2001, vol. 73, pp. 6047-6052.

Avseenko et al., "Immunoassay with Multicomponent Protein Microarrays Fabricated by Electrospray Deposition," Anal. Chem., 2002, vol. 74, pp. 927-933.

Delaney et al., "Inkjet printing of proteins," Soft Matter, 2009, vol. 5, pp. 4866-4877.

Han et al., "BioPen: direct writing of functional material at the point of care," Scientific Reports, 2014, vol. 4, Article No. 4872, pp. 1-5 DOI:10.1038/srep04872.

Helmja et al., "Fraction collection in capillary electrophoresis for various stand-alone mass spectrometers," Journal of Chromatography A, 2009, vol. 1216, pp. 3666-3673.

Jaworek et al, "Electrospraying route to nanotechnology: An overview," Journal of Electrostatics, 2008, vol. 66, pp. 197-219.

Jin et al., "Western Blotting Using Microchip Electrophoresis Interfaced to a Protein Capture Membrane," Anal. Chem., 2013, vol. 85, pp. 6073-6079.

Johnson et al., "A CE-MALDI Interface Based on the Use of Prestructured Sample Supports," Anal. Chem., 2001, vol. 73, pp. 1670-1675.

Kim et al., "Design and evaluation of single nozzle with a non-conductive tip for reducing applied voltage and pattern width in electrohydrodynamic jet printing (EHDP)," J. Micromech. Microeng., 2010, vol. 20, (7 pp).

Korkut et al., "Enhanced Stability of Electrohydrodynamic Jets through Gas Ionization," PRL, 2008, vol. 100, pp. 034503-1-034503-4.

Lu et al., "Coupling Sodium Dodecyl Sulfate-Capillary Polyacrylamide Gel Eletrophoresis with Matrix-Assisted Laser Desorption Ionization Time-of-Flight Mass Spectrometry via a Poly(tetrafluoroethylene) Membrane," Anal. Chem., 2011, vol. 83, pp. 1784-1790.

Magnusdottir et al., "Micropreparative capillary electrophoresis of DNA by direct transfer onto a membrane," Electrophoresis, 1997, vol. 18, pp. 1990-1993.

Morozov et al., "Electrospray Deposition as a Method to Fabricate Functionally Active Protein Films," Anal. Chem., 1999, pp. 1415-1420.

Morozov et al., "Electrospray Deposition as a Method for Mass Fabrication of Mono- and Multicomponent Microarrays of Biological and Biologically Active Substances," Anal. Chem., 1999, vol. 71, pp. 3110-3117.

Rejtar et al., "Off-Line Coupling of High-Resolution Capillary Electrophoresis to MALDI-TOF and TOF/TOF MS," Journal of Proteome Research, 2002, vol. 1(2), pp. 171-179.

Tracht et al., "Postcolumn Radionuclide Detection of Low-Energy β Emitters in Capillary Electrophoresis," Anal. Chem., 1994, pp. 2382-2389.

Uematsu et al., "Surface morphology and biological activity of protein thin films produced by electrospray deposition," Journal of Colloid and Interface Science, 2004, vol. 269, pp. 336-340.

Wei et al., "Electrospray sample deposition for matrix-assisted laser desorption/ionization (MALDI) and atmospheric pressure MALDI mass spectrometry with attomole detection limits," Rapid Commun. Mass Spectrom., 2004, vol. 18, pp. 1193-1200.

Zhang et al., "Capillary Electrophoresis Combined with Matrix-Assisted Laser Desorption/Ionization Mass Spectrometry; Continuous Sample Deposition on a Matrix-precoated Membrane Target, Journal of Mass Spectrometry," 1996, vol. 31, pp. 1039-1046.

Zhong et al., "Recent advances in coupling capillary electrophoresis-based separation techniques to ESI and MALDI-MS," Electrophoresis, 2014, vol. 35, pp. 1214-1225.

Derby , "Inkjet Printing of Functional and Structural Materials: Fluid Property Requirements, Feature Stability, and Resolution", Annu. Rev. Mater. Res. 40, 2010, pp. 395-414.

International Search Report and Written Opinion dated Apr. 4, 2017, for corresponding PCT Appln No. PCT/US2017/015657, 17 pages.

Martin et al., "Inkjet printing—the physics of manipulating liquid jets and drops", Engineering and Physics-Synergy for Success, IOP Publishing, Journal of Physics: Conference Series 105, 2008, pp. 1-14.

Anderson et al., "Western Blotting using Capillary Electrophoresis", Analytical Chemistry, 2011, pp. 1350-1355.

Gast et al., "The development of integrated microfluidic systems at GeSiM", Lab on a Chip, 3, 2003, pp. 6N-10N.

Jin et al., "Western Blotting Using Microchip Electrophoresis Interfaced to a Protein Capture Membrane", Analytical Chemistry 85(12), 2013, pp. 6073-6079.

Written Opinion dated Aug. 31, 2017 for PCT/US2017/015657, 14 pages.

Jin et al., "Multiplexed Western Blotting Using Microchip Electrophoresis", Analytical Chemistry, vol. 88, No. 13, 2016, pp. 6703-6710.

* cited by examiner

ANALYTE SEPARATOR WITH ELECTROHYDRODYNAMIC TAYLOR CONE JET BLOTTER

CROSS-REFERENCES TO RELATED APPLICATIONS

This application claims the benefit of U.S. Provisional Application No. 62/024,256, filed Jul. 14, 2014, which is hereby incorporated by reference in its entirety for all purposes.

STATEMENT AS TO RIGHTS TO INVENTIONS MADE UNDER FEDERALLY SPONSORED RESEARCH AND DEVELOPMENT

Not Applicable

BACKGROUND

1. Field of the Invention

Generally, this application relates to molecular biology and bioanalytical chemistry processes and apparatuses including testing means. Certain embodiments relate to devices, systems, and methods for preparing protein assays.

2. Background

Western blotting is a ubiquitous technique for identifying and quantifying specific proteins in complex biological samples. The proteins are separated using gel electrophoresis by their molecular weight (or isoelectric point), and then the proteins are transferred to a membrane, such as nitrocellulose or PVDF. The proteins on the membrane are then stained with antibodies of the targeted proteins for identification and/or confirmation of the proteins.

Capillary electrophoresis is sometimes an alternative to gel electrophoresis. Less touch labor is typically necessary, and smaller samples can be used. Microfluidic channels on a 'chip' have been studied as an extremely efficient version of capillary electrophoresis, and wicking the output of microfluidic channels directly onto a x-y translating membrane has been studied as an alternative to creating Western blots (U.S. Patent Application Publication No. US 2013/0213811 A1, published Aug. 22, 2013). Unfortunately, uneven wicking into the membrane has been found to cause adverse effects such as high background and inconsistent fluid flow. Further, the geometry must be carefully set up lest there be damage to the solid-support, damage to the microchip, and occasional loss of electrical current when the contact is interrupted.

There is a need in the art for improvements in sample preparation for Western blots, Northern blots, Southern blots, and other 1-dimensional or 2-dimensional membrane analysis methods.

BRIEF SUMMARY

Generally, devices, systems, and methods are described that separate a fluidic sample of proteins or other analyte and then transfer the separated analyte to a moving medium using an electrohydrodynamic (EHD) sprayer. An electrode charges the fluid by removing or adding electrons from molecules in the fluid and/or fluid from an auxiliary sheath fluid. The EHD sprayer then emits the charged fluid through an electrospray head, creating a Taylor cone and associated jet. Before the charged fluid in the jet repels into a mist, it hits a substrate in which the fluid is blotted. That is, a gap between the electrospray head and the substrate is small enough that the fluid is still in cohesive jet or stream when it hits the substrate. While the jet of liquid is transferring fluid to the substrate, the substrate translates in a direction perpendicular to the sprayer tip (i.e., laterally with respect to the sprayer tip) in order to keep the gap size constant. Alternatively, the sprayer tip can move (laterally) and the medium stays fixed.

In some embodiments in which electrophoresis is used for the separation, a conductor electrode used for electrophoresis is shared with a conductor electrode for the EHD sprayer. The upstream voltage for electrophoresis and substrate voltage for electrospraying are adjusted selected in relation to the common, shared conductor.

Multiple spray heads can be lined in a row and emit different analytes in multiple columns on the membrane. A lab-on-a-chip configuration, with multiple channels terminating in EHD sprayers, can shoot several lines of output from separation columns etched in the chip substrate.

Some embodiments of the present invention are related to an apparatus for separating and continuously blotting a fluid sample. The apparatus includes a separator with a fluid path filled with a separation matrix, the fluid path having an input end and an output end, the input end of the fluid path having an opening configured to accept a fluid sample for separation, an electrohydrodynamic (EHD) electrode in connection with the output end of the fluid path, the EHD electrode configured for imparting an electric charge to a fluid sample within the fluid path and creating a stream of charged fluid, a substrate positioned across a gap from the output end, a substrate electrode connected with the substrate, and a motor connecting the substrate to the separator, the motor configured to laterally and continuously move the substrate and separator with respect to each other.

The apparatus can include a third electrode coupled with the fluid path upstream of the output end of the fluid path, wherein the third electrode and EHD electrode are configured to apply an electric field within the fluid path for electrophoresis. The apparatus can include an adjunct tube with an output in fluidic contact with the output end of the fluid path, the adjunct tube configured to present a second fluid at the output end of the fluid path and entrain an output of the separation matrix with the second fluid. The fluid path can include a lumen of a capillary tube, and the adjunct tube can include a sheath surrounding a portion of the capillary tube.

The apparatus can include a pump configured to pump the second fluid through the adjunct tube. The apparatus can include a pump configured to load the fluid sample onto the fluid path. The gap can be a distance of about 0.5 mm to about 10 mm, including a distance of about 0.5 mm to about 3 mm. The gap can be less than that in which the stream of charged fluid begins to disperse into droplets. The gap can be configured to be greater than a height of a Taylor cone of charged fluid from the output end.

The separator can be selected from the group consisting of a capillary tube and a micro-fabricated chip. A voltage source can be operatively connected with at least one of the electrodes. A fluid sample can be present within the fluid path. The separation matrix can be selected from the group consisting of nanoparticles, beads, a gel, and macromolecules in solution. The gel can be selected from the group consisting of cross-linked polymers, an acrylamide gel, and an agarose gel. The nanoparticles can comprise silica spheres between about 1 nm and about 2000 nm in diameter arranged in a crystal structure. The separator can be adapted to move and the substrate is fixed, and/or the substrate can be adapted to move and the separator is fixed.

The substrate can have an axis of rotation, the axis having a center of rotation displaced from a target area for the charged fluid, the axis being parallel to the gap between the output end and the substrate such that rotating the substrate moves the substrate laterally. The apparatus can include a plurality of fluid paths with outputs coupled with respective EHD electrodes, the EHD electrodes configured parallel to one another, wherein the substrate is adapted to be moved perpendicular to a line between two of the outputs.

Some embodiments relate to a method for separating and blotting a fluid sample. The method includes providing a fluid path filled with a separation matrix, the fluid path having an input end and an output end, the input end of the fluid path having an opening configured to accept a fluid sample for separation, administering the fluid sample to the input end, separating analytes within the fluid sample, imparting an electrical charge to the fluid sample at the output end of the fluid path in order to charge the fluid sample into a charged fluid, causing a voltage potential across a gap between the output end and a substrate, the voltage potential sufficient to cause the charged fluid to form a Taylor cone and jet, moving the substrate with respect to the fluid path, and blotting the charged fluid of the jet onto the substrate, the blotting occurring during the moving.

The method can include generating an electric field between the input end and output end of the fluid path, the electric field helping to separate the analytes by electrophoresis. The method can include mixing sodium dodecyl sulfate (SDS) with the fluid sample, thereby preparing the fluid sample for SDS electrophoresis. The method can include applying pressure to the input end, thereby forcing the fluid sample through the fluid path by pressure. The method can include presenting a second fluid at the output end of the fluid path, and entraining an output of the separation matrix with the second fluid.

The method can include detecting an analyte on the substrate using a detection reagent. The detection reagent can comprise an antibody. The antibody can comprise a primary antibody and a secondary antibody. The fluid sample can be a biological sample selected from the group consisting of proteins, nucleic acids, and carbohydrates. The fluid sample can include a protein ladder mixture.

The charged fluid can be positively or negatively charged.

The method, devices, systems and other aspects, objects and advantages will become more apparent when read with the detailed description and figures which follow.

DETAILED DESCRIPTION

In general, embodiments enable the direct-blotting of proteins (or other molecules) by an electrohydrodynamic technique from a separation column onto a solid support for subsequent immuno-probing. The solid support moves with respect to the separation column, and liquid is transferred from the separation column to the solid support by electrospray techniques so that the solid support does not necessarily have to touch the separation column.

"Electrohydrodynamics" includes the study and application of fluid flow induced by an applied electric field, or as otherwise known in the art. An electrospray device is an example of an electrohydrodynamic application.

An "electrospray" includes techniques related to charging a fluid and expelling it so that it forms a Taylor cone and jet, or as otherwise known in the art. An electrospray can include devices that spray the charged fluid into a fine mist as well as devices that shoot a stream of charged fluid that does not have time to disperse into a mist before hitting an object, such as a substrate.

A technical advantage of using electrohydrodynamics is that there is no requirement for solid contact between a separation column output and a membrane substrate. This can alleviate problems such as high background, damage to the solid-support, damage to the microchip, inconsistent fluid flow, and occasional loss of electrical current when the contact is interrupted. Further, it generally simplifies the instrument design while being compatible with various separation techniques (e.g. chromatography, electrophoresis, etc.) and media (e.g. linear acrylamide, silica colloidal crystals, etc.).

A further technical advantage is that it enables high-resolution (spatial) blotting of molecules onto a solid support as they elute from a separation column. It also can work with wide variety of flow rates (e.g. 10 nL/min-10 uL/min), does not fragment (damage) biomolecules during the process, physically isolates the separation column from the solid support (no need to maintain liquid connection), and enables easy and fast control of the blotting process (i.e. turn on/off voltage potential, minimal "inertia" to stop/start). In some instances, it can be used to deliver antibodies and/or blocking reagents for low volume consumption (i.e. possible uses beyond separated samples).

Figure 1:
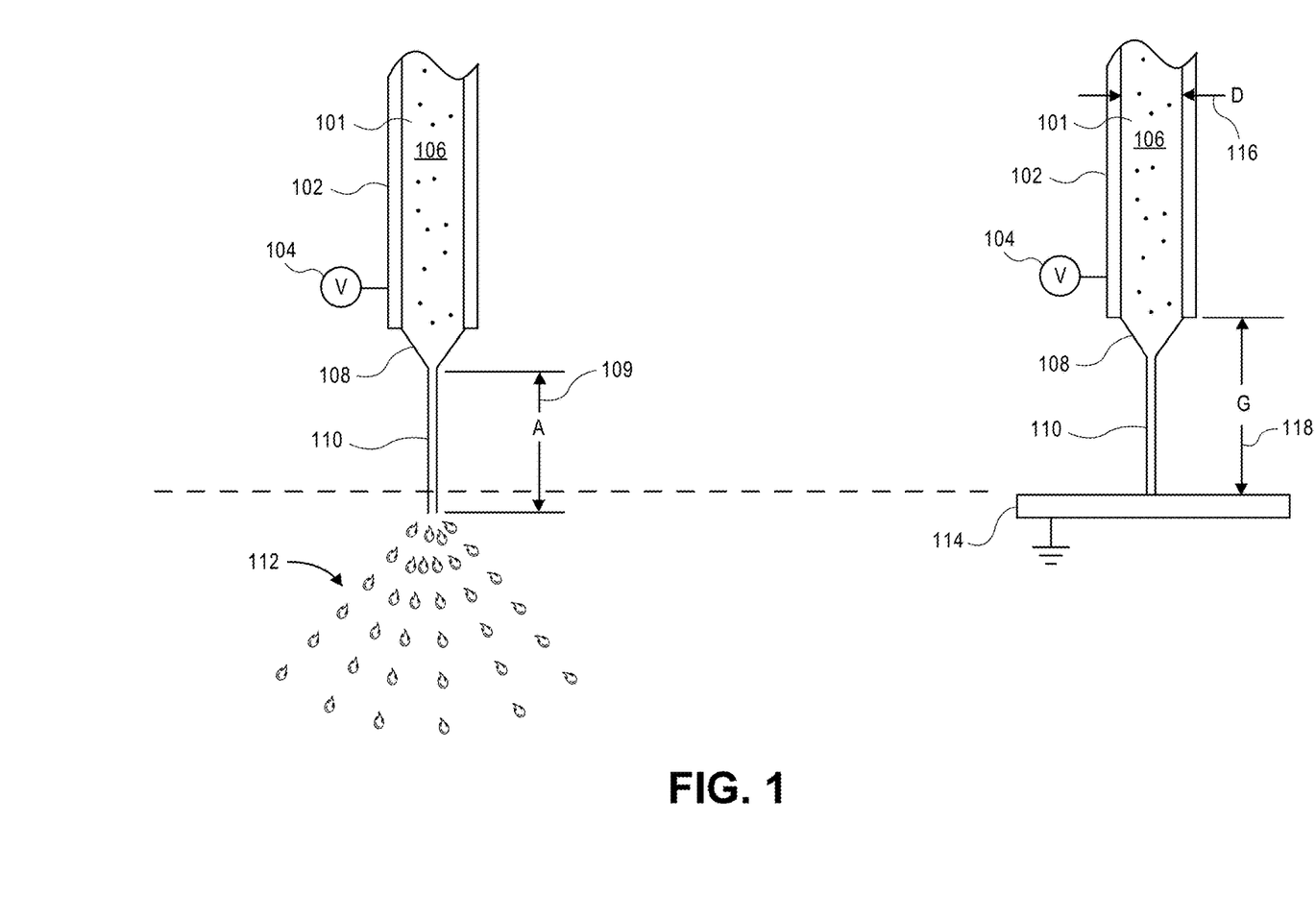
FIG. 1 compares a conventional electrosprayer with an electrospray device truncated by a substrate in accordance with an embodiment.

FIG. 1 illustrates a conventional electrospray apparatus dispersing fine droplets (on the left side of the figure) as well as an electrospray device with its jet truncated by a substrate (on the right side of the figure).

For traditional electrosprays, a positively charged electrode (i.e., an electrode missing many electrons) pulls electrons from molecules in a fluid (because of the voltage potential). This charges the molecules positively. Then, the positively charged molecules in the fluid are attracted out of the spray head toward a negatively charged electrode. Because of the balance of surface tension forces and electric stresses, the charged fluid forms a Taylor cone and jet. As the jet moves away from the Taylor cone, the positively charged molecules repel each other through Coulomb forces. At a certain point, the repulsion forces overcome the surface tension of the jet and break free, forming a spray plume of fine droplets.

Of course, the same holds true if the charges are reversed (and electrons are donated from the sprayer electrode to the molecules in the fluid to make them negatively charged).

In the figure, capillary 102 has lumen 101 that holds fluid 106, which is charged by voltage source 104. In the example, fluid 106 is deprived of electrons by voltage source 104 and becomes positively charged.

The voltage source creates a potential with a target (e.g. 1-10 kV). Fluid 106 exits the end of the capillary and forms Taylor cone 108. Jet 110 of fluid is emitted out of the apex of the Taylor cone 108. Simultaneously, the liquid sample 106 is subjected to a flow rate induced by pressure, such as a syringe pump. At distance A 109 from the apex of Taylor cone 108, jet 110 disperses into plume 112, which is a mist of fine droplets. Distance A 109 depends on the voltage potential set up by voltage source 104 between the end of capillary 102 and the ground, among other things. The droplets continue to break apart until evaporation completely eliminates the liquid surrounding the sample ions. As the droplets get smaller, the static charge repels them from one another causing the spray to diverge.

On the right hand side of the figure, substrate 114 intercepts jet 110 before it disperses. That is, gap G 118 is less than that in which stream 110 of charged fluid begins to disperse into droplets. The geometry can generally be determined based on diameter D 116 of capillary tube 103, the voltage potential between power source 104 and grounded substrate 114, and the viscosity, surface tension, conductivity, and relative permittivity of the fluid.

Embodiments using electrohydrodynamic blotting employ some of the same physics as an electrospray, but with differing goals for the application. In electrospray ionization (and deposition) it is intended that the sample be ionized into a gaseous state, whereas with blotting it is not necessary to ionize the sample directly or evaporate it out of solution. This allows the substrate to be placed closer to the Taylor cone. Preferably, the substrate would be located between the end of the cone and before droplet formation. This zone would enable the highest spatial resolution of blotting (the resolution may be adequate even with the spray plume).

Another major difference between electrospray dispersion and EHD blotting is the sample contents. When ionization and mass spectra are desired, there are strict requirements on the contents of the sample. For example, surfactants can be troublesome. For blotting, however, there is little-to-no requirement for sample ionization and almost no interest in the mass spectra. Therefore, sodium dodecyl sulfate (SDS; typically required for size separation) normally does not pose a problem.

Figure 2:
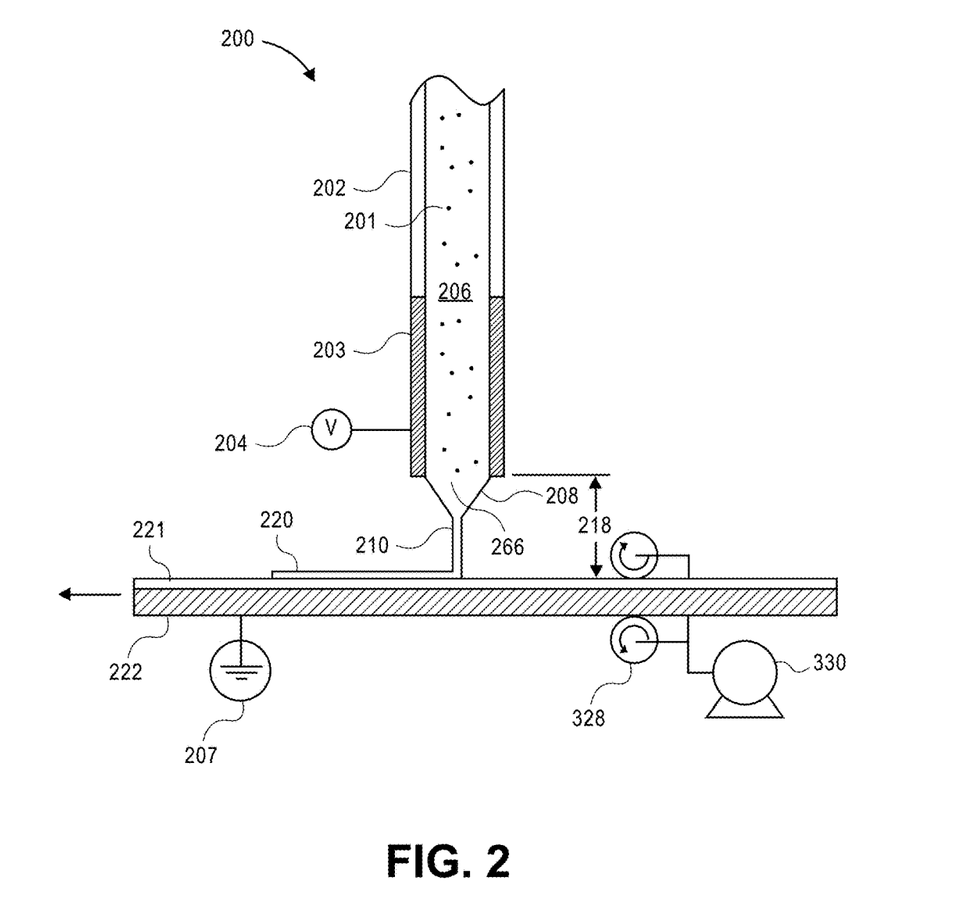
FIG. 2 illustrates an electrohydrodynamic (EHD) Taylor cone jet blotter with a moving substrate in accordance with an embodiment.

FIG. 2 illustrates an electrohydrodynamic (EHD) Taylor cone jet blotter with a moving substrate in accordance with an embodiment. In system 200, capillary 202 with lumen 201 carries fluid sample 206 to an output end 266 of the fluid path. There, electrode 203, connected with voltage source 204, imparts a charge to fluid sample 206, charging it. Based on a voltage potential between electrode 203 and substrate 222, which is connected to ground 207, the charged fluid sample is attracted across gap 218. It forms Taylor cone 208 and jet 210 before being deposited on substrate 222.

Substrate 222 is configured to move while the charged fluid is blotted on blotting portion 221 of substrate 222. Motor 330 turns rollers 328 in order to move substrate 222 in a direction that is perpendicular to capillary 202, that is laterally.

In other embodiments, the capillary may be configured to move while the substrate stays fixed. Either way, substrate 222 and capillary separator 202 move with respect to one another.

Figure 3:
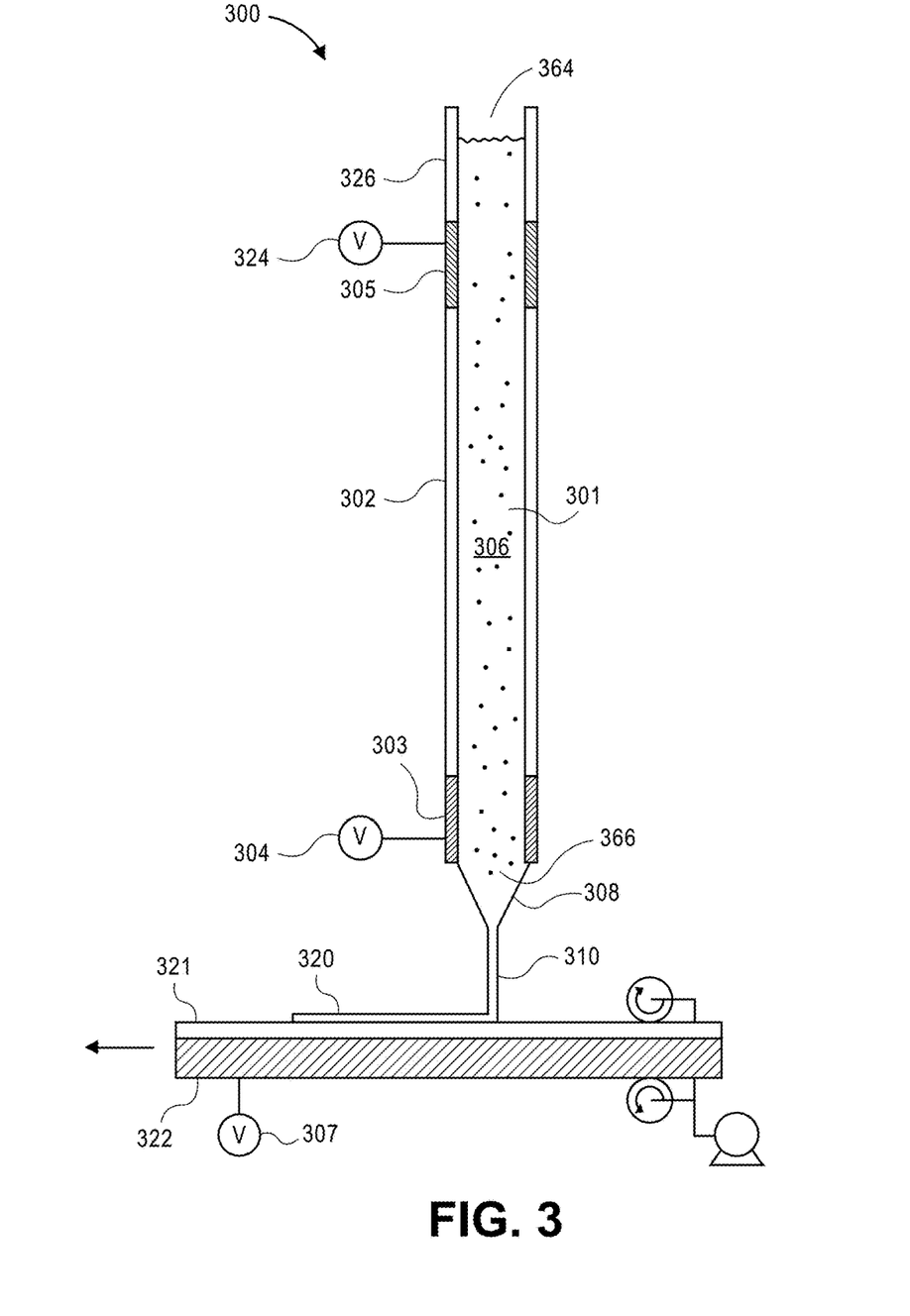
FIG. 3 illustrates electrophoresis separation with an electrohydrodynamic Taylor cone jet blotter in accordance with an embodiment.

FIG. 3 illustrates electrophoresis separation with an electrohydrodynamic Taylor cone jet blotter in accordance with an embodiment. In system 300, capillary 302 has fluid path 301 and two electrodes: a first, electrohydrodynamic (EHD) electrode 303 connected with output end 366 of fluid path 301; and another electrode 305 upstream from output end 366. In the exemplary figure, electrode 305 is below input end 364. The region of capillary 302 above electrode 305 is an entryway region 326.

Fluid path 301 is filled with a separation matrix of acrylamide gel. A voltage source holds voltage 324 at a different voltage from voltage 304. The difference in voltages causes analytes in the fluid sample to separate from one another, a technique known as electrophoresis.

"Electrophoresis" includes the induced motion of particles suspended in a fluid by an electric field, or as otherwise known in the art. Electrophoresis of positively charged particles (cations) is often called cataphoresis, while electrophoresis of negatively charged particles (anions) is often called anaphoresis.

A "protein ladder" includes a mixture of known-kDa proteins that can be used for calibrating electrophoresis and other separation techniques. Comparison between the protein ladder and a sample can help an analyst determine unified atomic mass units (i.e., Daltons) of items of interest in the sample. A protein ladder can be employed in separation column 302.

Sodium dodecyl sulfate (SDS) can be mixed with the fluid sample before entering it into the separation matrix, such as in region 326 or before, thereby preparing the fluid sample for SDS-denatured electrophoresis The central capillary can be filled with nanoparticles, beads, a gel (e.g., acrylamide gel, agarose gel), macromolecules in a solution, colloidal crystal (1 nm to about 2000 nm in diameter), or other separation matrix.

At the bottom of the figure, substrate electrode 322 is connected with substrate 321, which moves laterally. Voltage source 307, which connects to electrode 322, has a positive charge of 1 kV to 10 kV in relation to electrode 303. However, it can have negative voltages and other magnitudes as well.

In the exemplary embodiment, substrate 321 moves to the left while the capillary tube is fixed. Output from the separation matrix forms Taylor cone 308 and jet 310. The jet extends across a gap between the tip of the capillary tube, effectively an EHD 'sprayer,' and is deposited onto substrate 321.

The deposition occurs continuously while the substrate moves steadily to the left. By adjusting the speed of the substrate and voltage of the electrophoresis, a large resolution of separation can be obtained.

Notably in this embodiment, three electrodes are present. The top electrode is connected with the capillary and is for electrophoresis. Typically, it has a negative charge of 1 kV to 10 kV in relation to the second electrode. However, it can have positive voltages and other magnitudes as well. The second (middle) electrode is connected with the output end of the capillary and is for both electrophoresis and electrohydrodynamic spraying. The second electrode can be grounded or held at a particular voltage. The voltage difference between the top electrode and second electrode is what creates an electric field in the fluid path of the capillary and electrokinetically drives the motion of dispersed particles in the fluid sample. The third (bottom) electrode is held at a value that induces the liquid exiting the output end 366 of the fluid path to form a Taylor cone and jet. The jet contacts substrate 321 and blots upon the substrate while the substrate moves.

Figure 4:
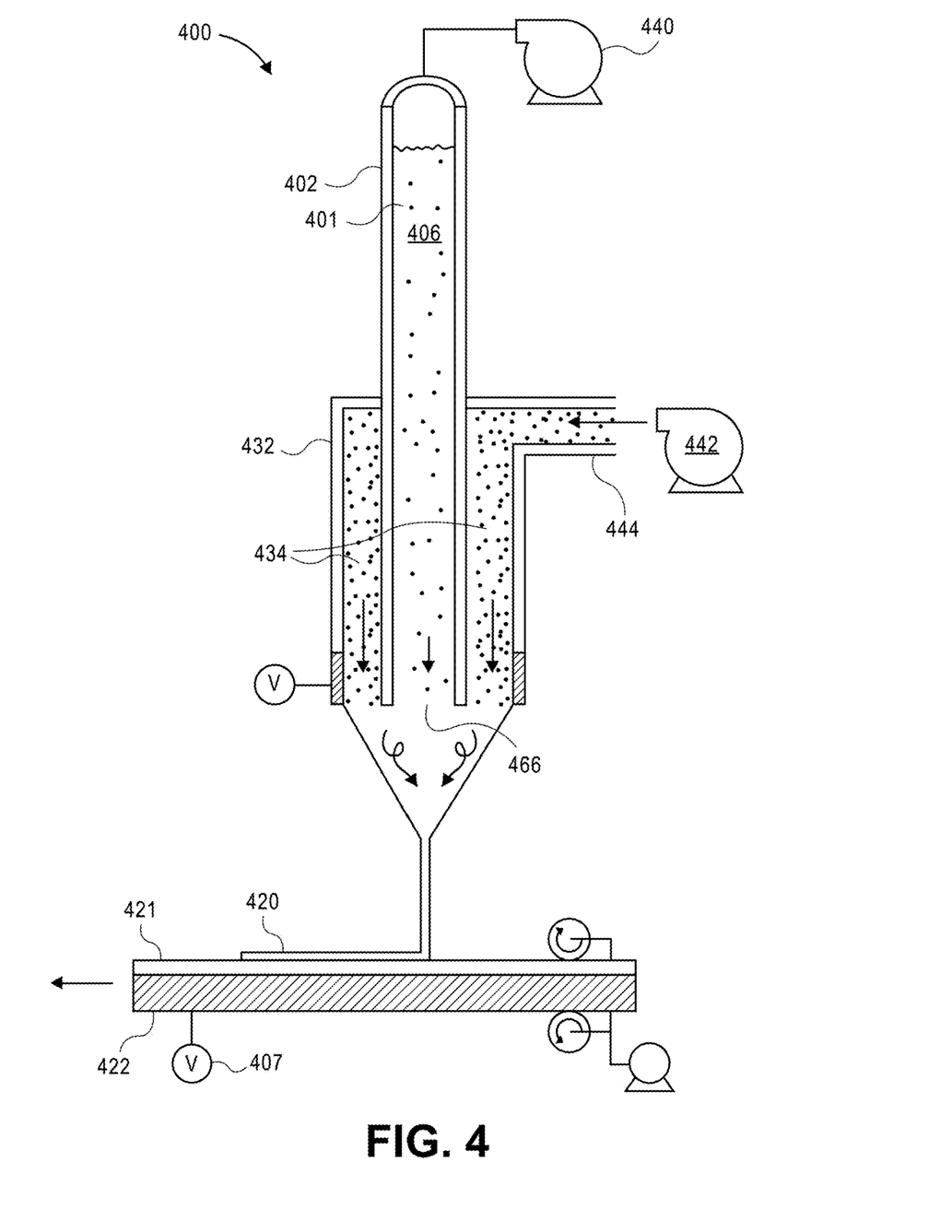
FIG. 4 illustrates high-pressure liquid chromatography (HPLC) separation with an electrohydrodynamic Taylor cone jet blotter in accordance with an embodiment.

FIG. 4 illustrates high-pressure liquid chromatography (HPLC) separation with an electrohydrodynamic Taylor cone jet blotter in accordance with an embodiment.

Since one may intend to blot size-separated biomolecules, one can use a sheath flow to carry the molecules, leaving behind the separation matrix. If using the silica colloidal crystal as the separation matrix in the separation column, it can be advantageous as there will be little-to-no risk of losing the separation matrix into the sheath flow via mixing/diffusion.

In system 400, capillary 402 with fluid path 401 is pressurized by pump 440 in order to move fluid sample 406 through a separation matrix.

Adjunct tube 432 concentrically surrounds the lower portion of the capillary tube in an annular fashion as a "sheath." The adjunct tube delivers a shaping fluid, such as an aqueous and organic mixture solution, to output end 466 of fluid path 401 of capillary tube 402. Pump 422 pressurizes the sheath flow so that it exits the sheath tube at an acceptable rate. The shaping fluid entrains output from the capillary tube, establishing enough flow for there to be a Taylor cone and associated jet of charged fluid.

In this embodiment, the sample fluid blots onto a conductive, or semi-conductive, surface of the substrate 421. Below this surface is substrate electrode 422, which is held at a voltage potential by voltage source 407 with respect to the electrospray tip in order to induce the Taylor cone and jet. Substrate 421 moves to the left at a fixed speed while the separated fluid sample is deposited.

In some embodiments with a pressurized fluid path, no adjunct flow is necessary. Separation proceeds via pressure through the separation tube as opposed to electrophoresis. Pressure is applied at the top of the separation capillary, and the bottom, output end of the separation capillary is kept at atmospheric pressure. The separated sample fluid exits at the end of the capillary and is charged (or grounded) at the tip by an effective EHD sprayer tip. A Taylor cone and jet are formed, as before, and they are attracted to the oppositely charged substrate below.

Figure 5:
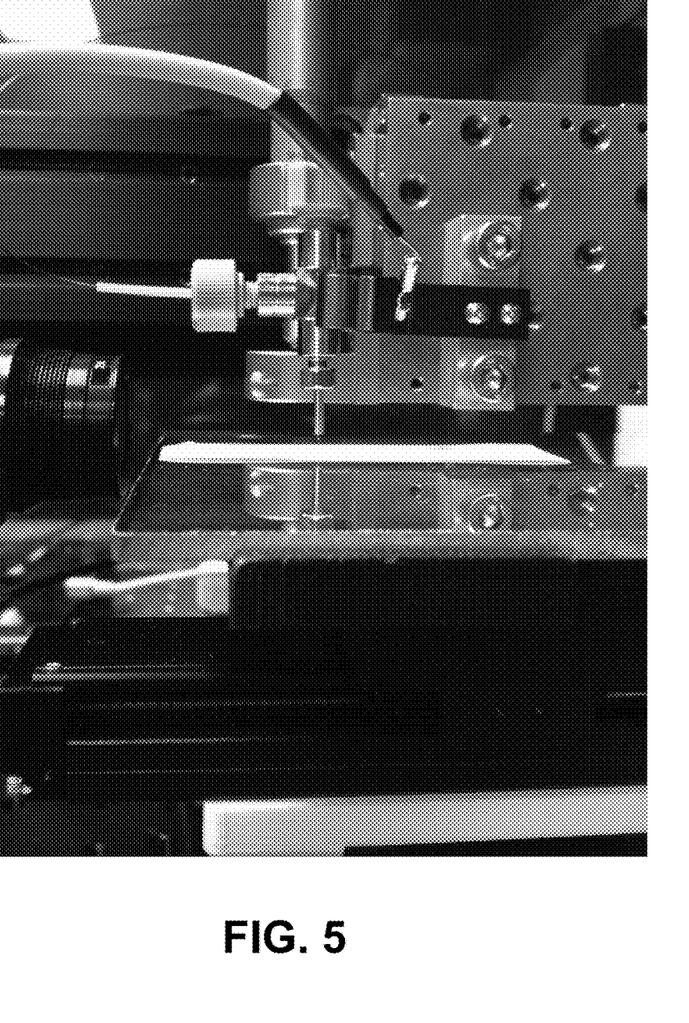
FIG. 5 is a picture of a prototype apparatus in accordance with an embodiment.

FIG. 5 is a picture of a prototype apparatus in accordance with an embodiment. A capillary separation tube is set in place over a substrate at a fixed distance (i.e., a gap). The substrate is mounted on translating support that is moved by stepper motors. The substrate includes a conductive plate that is held at a fixed voltage and a nonconductive membrane that rests atop the conductive plate.

An adjunct, sheath flow is supplied from a tube that comes in horizontally from the left. The adjunct flow turns downward within the T fitting and travels downward through a channel that surrounds the separation capillary. The adjunct flow continues through a sheath, which surrounds the separation capillary until just before the end of the separation capillary. In the picture, the separation capillary is shown poking out the bottom of the larger sheath tube, just above the membrane.

An electrical wire is connected to a metal clamp that holds the T fitting. This allows the conductive metal T fitting, and the metal sheath that is electrically coupled to it, to be held at a voltage. Another electrical wire connects to the conductive portion of the substrate. The difference in voltages between the sheath and substrate charges the sheath flow and mixed output from the separation capillary and promotes the Taylor cone and jet of the charged fluid that drops to the substrate across the gap.

Figure 6:
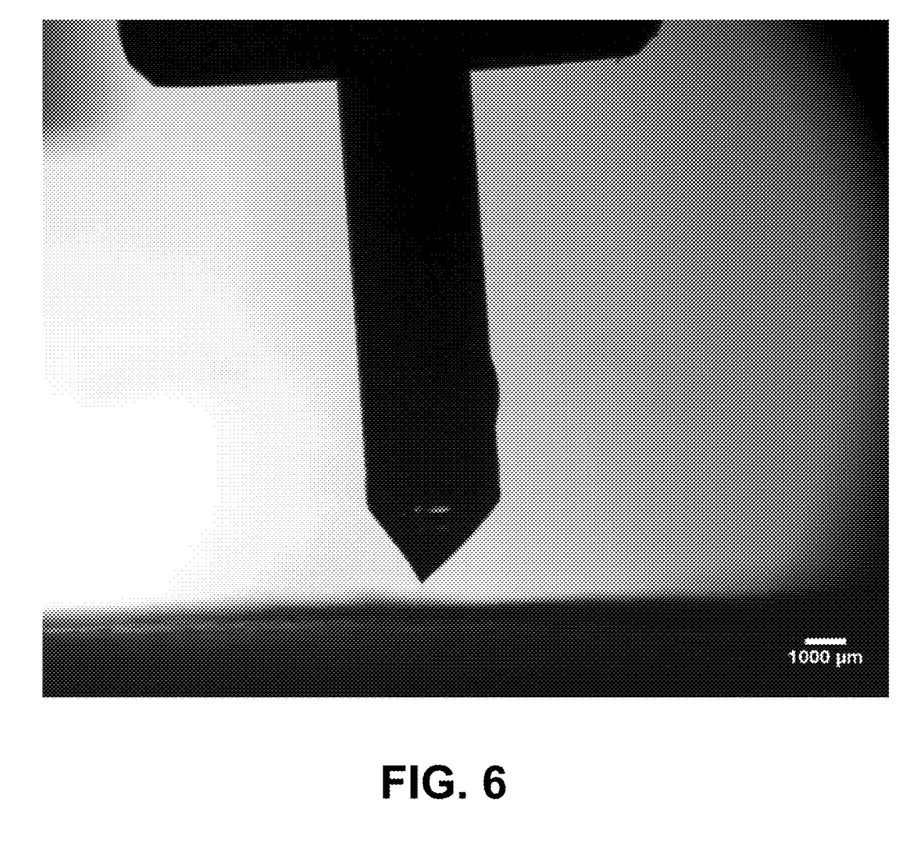
FIG. 6 is a close up picture of Taylor cone jet from the prototype apparatus of FIG. 5.

FIG. 6 is a close up picture of Taylor cone jet from the prototype apparatus of FIG. 5. For this example, the flow rate was 5 µl per minute, the voltage between the EHD spray head and substrate was −1500 V, and the height of the spray tip from the substrate was approximately 1.0 mm.

As evident from the photograph, a stable cone jet is formed with a thin jet at the end, and no dispersion of the jet occurs before it hits the substrate medium and is blotted thereon.

Gap distances of between about 0.5 mm to about 10 mm, preferably about 0.5 mm to about 3 mm, produce acceptable blotting. A gap that is less than that in which the stream of charged fluid begins to disperse into droplets is a gap that may work. The gap may be greater in height than a Taylor cone of charged fluid from the EHD sprayer.

In some embodiments, a fluid sample flows in the fluid path at a rate of 10 nL/min to 10 µL/min.

Figure 7:
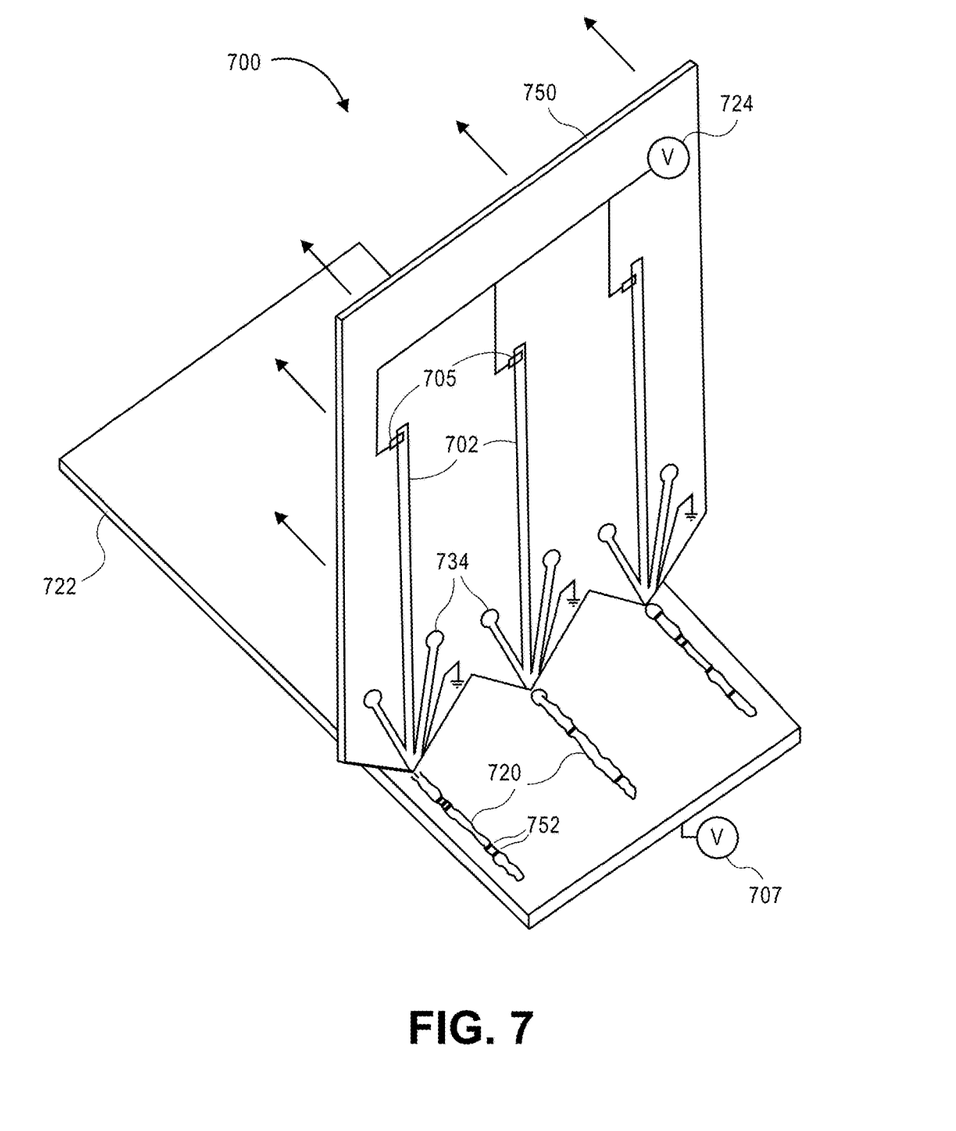
FIG. 7 is a perspective illustration of lab-on-a-chip based electrohydrodynamic spray blotters in accordance with an embodiment.

FIG. 7 is a perspective illustration of multiple microchip-based electrohydrodynamic spray blotters in accordance with an embodiment. In system 700, a single biological microchip 750 has three separation channels 702 that are etched into it, each separation channel terminating into a sharp, chamfered tip. Electrodes at each tip are grounded, while electrodes 705 at the top of each separation chamber are held at a constant voltage.

Sheath flows are provided by lines 734. The sheath flows entrain fluid sample with separated analytes. The combined flows are charged by the voltage potential between the grounded tips and voltage source 707 of substrate 722.

In the exemplary embodiment, microchip 750, and thus the EHD spray tips at the bottom of the chamfered tips, are moved perpendicularly to a line between the spray tips, depositing three even lines of separated samples on the substrate below. The chip does not necessarily need to be perpendicular to substrate 722 as shown. Substrate 722 is held at a voltage with respect to the tips of the spray heads.

More or fewer separation channels can be used, including hundreds of channels in a row on a single chip for massively parallel applications.

Figure 8:
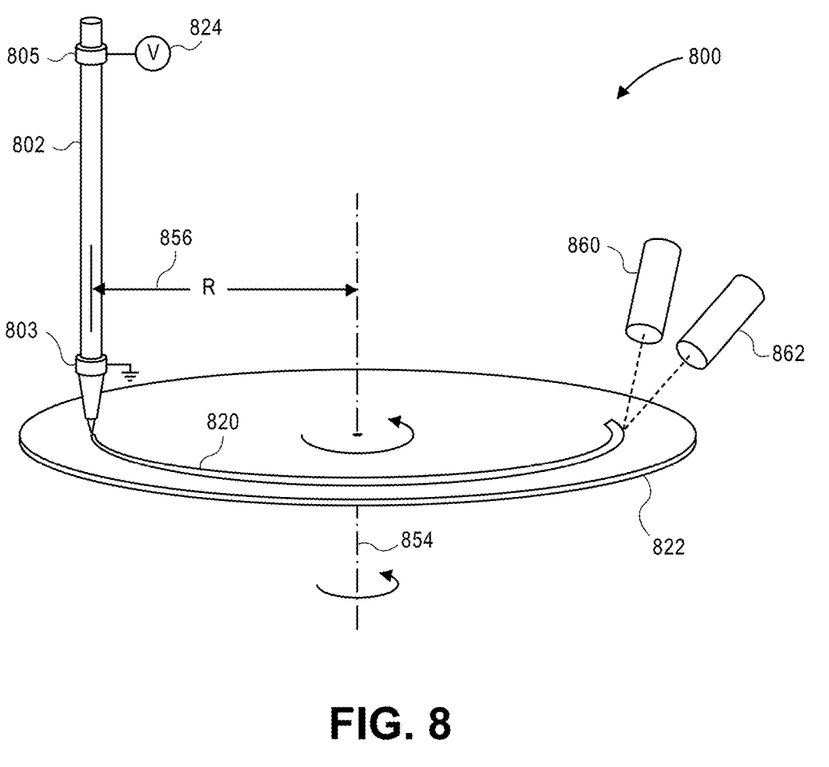
FIG. 8 is a perspective illustration of a turntable apparatus for mass spectroscopy in accordance with an embodiment.

FIG. 8 is a perspective illustration of a turntable apparatus for mass spectroscopy in accordance with an embodiment. Electrophoresis separation capillary 802 includes electrodes 805 and 803 at opposite ends. An electric potential is held between the electrodes by power supply 824 for electrophoresis.

An EHD spray head of capillary 802 is suspended over turntable 822. Turntable 822 is held at a voltage potential from electrode 803 of the separation capillary. While turntable 822 rotates around axis 854, separated sample fluid is emitted from the electrospray head onto the turntable, producing a track 820.

The turntable substrate can include a layer of silica colloidal nanoparticles or other neutral substrate compatible with matrix-assisted laser desorption/ionization (MALDI).

At an opposite end of the turntable, a MALDI/mass spectrometer laser 860 and detector 862 are aligned to perform matrix-assisted laser desorption/ionization. Thus, as output from the separation tube is deposited on the turntable, the track of deposited material is analyzed by a MALDI apparatus without human intervention.

Figure 9:
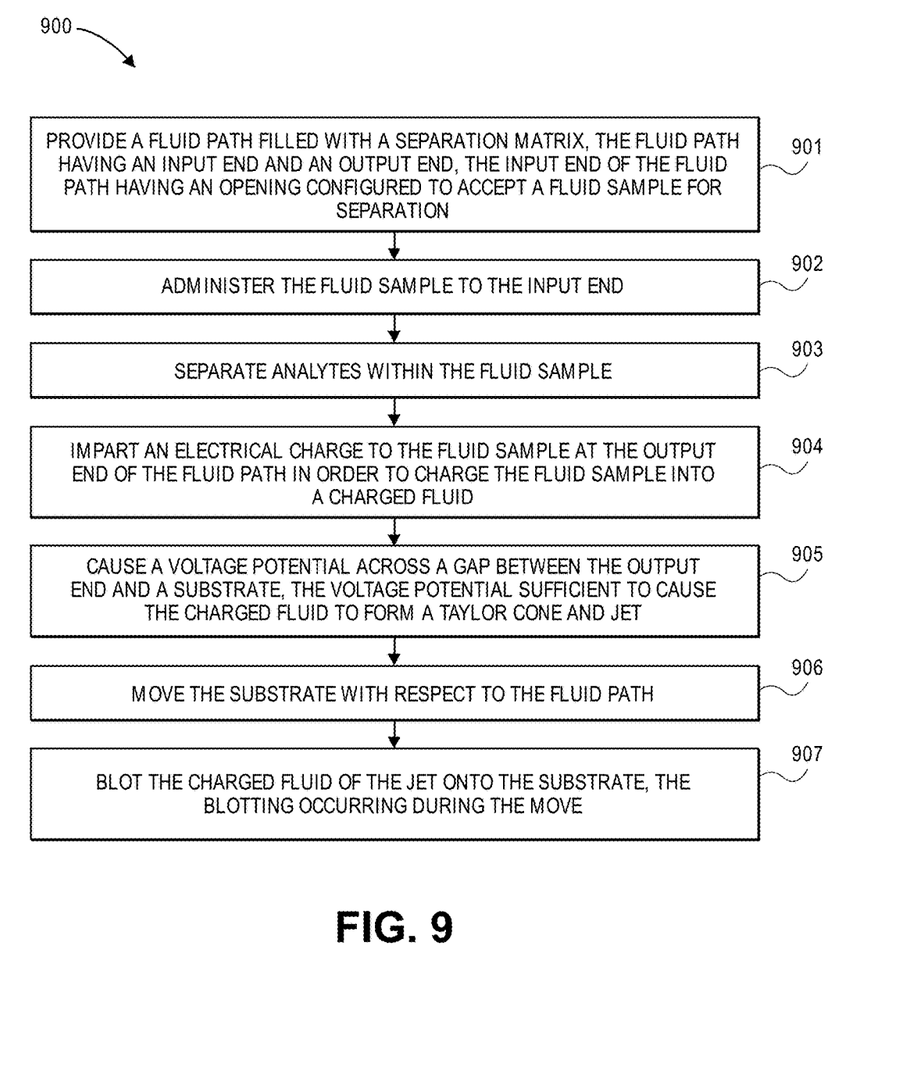
FIG. 9 is a flowchart illustrating a process in accordance with an embodiment.

FIG. 9 is a flowchart illustrating a process 900 in accordance with an embodiment. In operation 901, a fluid path filled with a separation matrix is provided. The fluid path has an input end and an output end. The input end of the fluid path has an opening configured to accept a fluid sample for separation. In operation 902, the fluid sample is administered into the input end of the fluid path. In operation 903, analytes within the fluid sample are separated. In operation 904, an electric charge is imparted to the fluid sample at the output end of the fluid path in order to charge the fluid sample into a charged fluid. In operation 905, a voltage potential across a gap between the output end and a substrate is caused, the voltage potential sufficient to cause the charged fluid to form a Taylor cone and jet. In operation 906, the substrate is moved with respect to the fluid path. In operation 907, the charged fluid of the jet is blotted onto the substrate, the blotting occurring during the movement of the substrate.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications, websites, and databases cited herein are hereby incorporated by reference in their entireties for all purposes.

What is claimed is:

1. An apparatus for separating and blotting a fluid sample, the apparatus comprising:
   a separator with a separator fluid path filled with a separation matrix, the separator fluid path having an input end and an output end, the input end of the separator fluid path having an opening configured to accept a fluid sample for separation;
   an electrohydrodynamic (EHD) electrode in connection with and proximate to the output end of the separator fluid path;
   a substrate positioned across an air gap from the output end, wherein the gap is a distance of about 0.5 mm to about 1 mm;
   a substrate electrode connected with the substrate; and
   a motor connecting the substrate to the separator, the motor configured to laterally and continuously move the substrate and separator with respect to each other,
   wherein the EHD electrode is configured for imparting an electric charge to a fluid sample within the separator fluid path and creating a Taylor cone and stream of charged fluid across the air gap to the substrate.

2. The apparatus of claim 1, further comprising:
   a third electrode proximate to the input end of the separator fluid path,
   wherein the third electrode and EHD electrode are configured to apply an electric field within the separator fluid path for electrophoresis.

3. The apparatus of claim 1, further comprising:
   an adjunct fluid path with an output in fluidic contact with the output end of the separator fluid path, the adjunct fluid path configured to present a second fluid at the output end of the separator fluid path and entrain an output of the separation matrix with the second fluid.

4. The apparatus of claim 3, wherein the separator fluid path includes a lumen of a capillary tube, and the adjunct fluid path includes a sheath surrounding a portion of the capillary tube and having an end aligned with an end of the capillary tube.

5. The apparatus of claim 3, the apparatus further comprising:
   a pump configured to pump the second fluid through the adjunct fluid path.

6. The apparatus of claim 1, wherein the gap is configured to be greater than a height of a Taylor cone of charged fluid from the output end and less than that in which the stream of charged fluid begins to disperse into droplets.

7. The apparatus of claim 1, wherein the separator is selected from the group consisting of a capillary tube and a micro-fabricated chip.

8. The apparatus of claim 1, further comprising:
   a voltage source operatively connected with at least one of the electrodes.

9. The apparatus of claim 1, further comprising:
   a fluid sample within the separator fluid path.

10. The apparatus of claim 1, wherein the separation matrix is selected from the group consisting of nanoparticles, beads, a gel, and macromolecules in solution.

11. The apparatus of claim 10, wherein the separation matrix comprises nanoparticles, and the nanoparticles comprise silica spheres between about 1 nm and about 2000 nm in diameter arranged in a crystal structure.

12. The apparatus of claim 10, wherein the gel is selected from the group consisting of cross-linked polymers, an acrylamide gel, and an agarose gel.

13. The apparatus of claim 1, wherein the separator is adapted to move and the substrate is fixed.

14. The apparatus of claim 1, wherein the substrate is adapted to move and the separator is fixed.

15. The apparatus of claim 1, wherein the substrate has an axis of rotation, the axis having a center of rotation displaced from a target area for the charged fluid, the axis being parallel to the gap between the output end and the substrate such that rotating the substrate moves the substrate laterally.

16. The apparatus of claim 1, wherein the apparatus comprises a plurality of separator fluid paths with outputs coupled with respective EHD electrodes, the EHD electrodes configured parallel to one another, wherein the substrate is adapted to be moved perpendicular to a line between two of the outputs.

17. The apparatus of claim 1, the apparatus further comprising:
   a pump configured to load the fluid sample onto the separator fluid path.

18. The apparatus of claim 1, wherein the EHD electrode is located at the output end of the separator fluid path.

* * * * *